United States Patent
Matriano et al.

(10) Patent No.: US 6,749,575 B2
(45) Date of Patent: Jun. 15, 2004

(54) METHOD FOR TRANSDERMAL NUCLEIC ACID SAMPLING

(75) Inventors: James A. Matriano, Mountain View, CA (US); Michel J. N. Cormier, Mountain View, CA (US)

(73) Assignee: Alza Corporation, Mountain View, CA (US)

(*) Notice: Subject to any disclaimer, the term of this patent is extended or adjusted under 35 U.S.C. 154(b) by 0 days.

(21) Appl. No.: 09/933,647

(22) Filed: Aug. 20, 2001

(65) Prior Publication Data

US 2003/0036710 A1 Feb. 20, 2003

(51) Int. Cl.[7] ............................................... A61B 10/00
(52) U.S. Cl. ..................... 600/564; 600/570; 600/572; 600/573; 600/583
(58) Field of Search ................................. 600/562, 564, 600/565, 569, 570, 571, 572, 573, 583, 575, 576

(56) References Cited

U.S. PATENT DOCUMENTS

| | | |
|---|---|---|
| 3,964,482 A | 6/1976 | Gerstel et al. ............... 128/260 |
| 5,161,532 A | 11/1992 | Joseph ........................ 128/635 |
| 5,250,023 A | 10/1993 | Lee et al. ...................... 604/20 |
| 5,279,544 A | 1/1994 | Gross et al. .................... 604/20 |
| 5,320,607 A | 6/1994 | Ishibashi ..................... 604/115 |
| 5,582,184 A | 12/1996 | Erickson et al. ............ 128/763 |
| 5,682,233 A | 10/1997 | Brinda ........................ 356/246 |
| 5,746,217 A | 5/1998 | Erickson et al. ............ 128/760 |
| 5,820,570 A | 10/1998 | Erickson et al. ............ 600/573 |
| 6,080,172 A * | 6/2000 | Fujiwara et al. ............. 606/166 |
| 6,091,975 A | 7/2000 | Daddona et al. ............ 600/345 |
| 6,440,096 B1 * | 8/2002 | Lastovich et al. ............. 604/27 |
| 2002/0177788 A1 * | 11/2002 | Hodges et al. ............... 600/583 |

FOREIGN PATENT DOCUMENTS

| | | | |
|---|---|---|---|
| WO | WO97/48440 | 12/1997 | ............ A61N/1/30 |
| WO | WO97/48441 | 12/1997 | ............ A61N/1/30 |
| WO | WO98/28037 | 7/1998 | ............ A61M/1/30 |
| WO | WO 0035530 | 6/2000 | |
| WO | WO01 41863 | 6/2001 | .......... A61M/37/00 |

OTHER PUBLICATIONS

Saiki, et al., Primer–directed Enztnaic Amplication of DNA with a Thermosable DNA Polymerase, Scienc, 2390:487 1988.
Saiki, et al., HLA–DQA1 with Allele Specific Oligonucleotide Probes, Nature, vol. 324, pp 163–166.

* cited by examiner

*Primary Examiner*—Eric F. Winakur
*Assistant Examiner*—Jonathan Foreman

(57) ABSTRACT

A minimally invasive transdermal nucleic acid sampling method comprises piercing through the outermost layer of the skin and into the underlying epidermis with a plurality of microprojections. Living skin cells in the underlying epidermis are disrupted, causing them to release their contents including their nucleic acids (i.e., DNA, RNA, fragments thereof or other polynucleic acid material found in the nucleii and/or mitochondria of cells). The nucleic acid is collected on the surfaces of the microprojections and/or in a separate nucleic acid collection reservoir. The collected nucleic acid is then analyzed using standard polymerase chain reaction (PCR) techniques. Optionally a suction device applies a partial vacuum through openings in the microprojection member to the microcuts in the skin for enhanced efflux of intracellular and extracellular (i.e., body) fluids containing the nucleic acid.

9 Claims, 2 Drawing Sheets ns for the purposes of this description.

METHOD FOR TRANSDERMAL NUCLEIC ACID SAMPLING

FIELD OF THE INVENTION

This application claims benefit under 35 U.S.C. 119(e) to U.S. Provisional Patent Application No. 60/227,675, filed Aug. 24, 2000.

The present invention relates to nucleic acid (e.g., DNA or RNA) sampling. More particularly, this invention relates to transdermal nucleic acid sampling. The present invention uses skin-piercing microprojections to pierce skin cells and affect transdermal nucleic acid sampling.

BACKGROUND OF THE INVENTION

DNA testing is presently performed by blood sampling or tissue swabbing followed by polymerase chain reaction (PCR) amplification of the DNA and then analysis of the amplified DNA. Blood sampling using a syringe is invasive and painful. Tissue swabbing is inconvenient and uncomfortable for many patients. One common procedure for sampling DNA uses buccal mucosal tissue samples obtained by rotating cyto brushes vigorously along the inside of the cheek for about 30 seconds.

There have been many attempts to enhance transdermal flux by mechanically puncturing the skin prior to transdermal drug delivery. See for example U.S. Pat. Nos. 5,279,544 issued to Gross et al., 5,250,023 issued to Lee et al., and 3,964,482 issued to Gerstel et al. These devices utilize solid and hollow microprojections to pierce the outer layer of the skin.

There have also been attempts to sample body analytes (e.g., glucose) contained in interstitial fluid using devices having similar skin-piercing microprojections. The analyte content in the interstitial fluid is then correlated with that in the blood. See for example, Cormier et al WO 97/48441; Joseph, U.S. Pat. No. 5,161,532; Erickson et al., U.S. Pat. No. 5,582,184; Brinda, U.S. Pat. No. 5,682,233; Erickson et al., U.S. Pat. No. 5,746,217 and Erickson et al., U.S. Pat. No. 5,820,570. Daddona et al. U.S. Pat. No. 6,091,975 provides a diagnostic device having stratum corneum-piercing microprojections. Electrochemical sensors are placed directly on the microprojections for sensing/measuring body analyte concentrations such as blood glucose concentration. One of the advantages of sampling interstitial fluid is that the wound created in the skin is not as deep as the wound needed for blood sampling. Thus, interstitial fluid sampling using such stratum corneum piercing microprojections is generally considered less invasive than blood sampling.

However, there is still a need for less invasive sampling of nucleic acids for the purposes of genetic testing (e.g., paternity testing, matching blood/semen samples to individuals in police/criminal detective work), medical diagnostics (e.g., screening patients for the presence of a disease and/or for predisposition towards disease such as heart disease), and the like.

DESCRIPTION OF THE INVENTION

The present invention provides a method for transdermal DNA sampling using a reproducible, high volume production, low-cost device. The invention comprises piercing through the outermost layer (i.e., the stratum corneum layer) of the skin and into the underlying epidermis layer, or into both the epidermis and dermis layers, with a plurality of microprojections. Individual skin cells within the epidermis/dermis layers are pierced, causing the cellular contents, including the cells' nucleus and its nucleic acids, to be released. The nucleic acids are coated onto the surfaces of the microprojections and/or absorbed into an absorbant coating on the microprojections. The microprojections typically have a length of less than about 0.4 mm and a width and thickness which is even smaller.

The method of the present invention can also be used to extract and sample nucleic acids released into the skin's interstitial fluid. As before, the outermost stratum corneum layer of the skin is pierced to form pathways through which the interstitial fluid, containing the nucleic acids, is withdrawn (i.e., sampled). Optionally, the sampling device used with this embodiment of the present invention can apply a partial vacuum (also referred to herein as "negative pressure") to the microcut skin. The negative pressure causes interstitial fluid to efflux from the microcuts. The interstitial fluid is collected, the nucleic acids contained therein is amplified using standard polymerase chain reaction (PCR) techniques, and then the amplified nucleic acids are analyzed.

In one aspect of the invention, the device for piercing the skin comprises a sheet having a plurality of openings therethrough, and a plurality of microprojections integral therewith and extending downward (i.e., in a direction toward the skin) therefrom. The optional negative pressure driven device applies a partial vacuum (i.e., suction) to the microcuts through the openings in the sheet.

MODES FOR CARRYING OUT THE INVENTION

Figure 4:
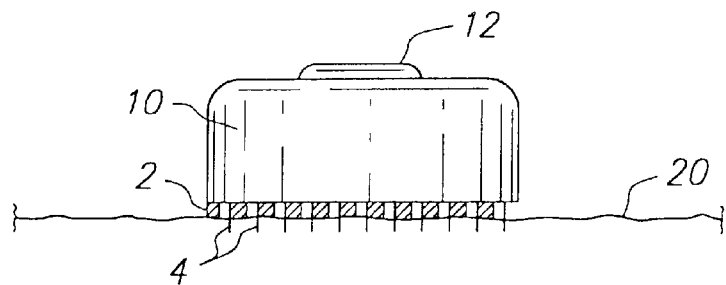
FIG. 4 is a side view of an optional negative pressure driven device with a microprojection DNA-sampling array shown in section.

The present invention provides a bloodless and pain free method of obtaining a nucleic acid sample from the skin. As used herein, the term "nucleic acid(s)" is used broadly to include DNA (i.e., deoxyribonucleic acid), DNA fragments, RNA (ribonucleic acid), RNA fragments, chromosomes, genes, and any other polynucleic acid sequence, or portion thereof, found in the nucleii and/or mitochondria of cells.

The skin is pierced with at least one, preferably a plurality and more preferably a multiplicity of, tiny stratum corneum piercing microprojections. Although the present invention is not limited to microprojections of any size, shape or configuration, in order for the sampling to be painless and bloodless, the microprojections should pierce into the skin to a depth of about 25 $\mu$m to about 400 $\mu$m, and preferably to a depth of about 50 $\mu$m to about 300 $\mu$m. Piercing to this depth with a plurality of microprojections ensures little if any bleeding, no significant sensation (pain) and further ensures that the blades will penetrate through the outermost stratum corneum layer of dead cells and into the epidermis layer, or into both the epidermis and dermis layers, which contain live skin cells. The piercing can be accomplished by impacting the microprojections against the skin surface using a device of the type disclosed in FIGS. 22 and 23 of Trautman et al., WO 01/41863 or using a conventional spring-loaded device of the type used to drive a lancet into the skin for blood droplet sampling.

Upon piercing into the epidermal layer, the microprojections, which are typically large in relation to the typical 20 $\mu$m diameter of living epidermal skin cells, will puncture and/or break apart a number of skin cells in the epidermal layer, or in both the epidermal and dermal layers, causing those cells to release their contents. This causes the skin cells' nucleii, and/or the nucleic acids originally contained in the skin cells' nucleii, to be released into the skin's extracellular fluid (also called interstitial fluid). This body fluid is coated onto the surfaces of the skin-piercing microprojections or absorbed into an absorbant coating on the microprojections. As a result, the cells' nucleic acids become coated or absorbed on the skin piercing microprojections. The skin piercing microprojections are typically made from either metal, plastic or silicon, any of which materials can be suitably coated with intracellular (from the ruptured skin cells) and extracellular body fluids, including the nucleic acids of the ruptured cells. Once the nucleic acid-containing fluids are coated onto the surfaces of the microprojections, the microprojections are removed from the skin, and the nucleic acid is collected for PCR amplification and later analysis. With typical metal, plastic or silicon based microprojections, the nucleic acid sample can simply be collected by immersing/incubating the microprojection in sterile water, optionally with surfactants, buffers and proteases. The target gene(s) in the DNA and/or RNA containing solution is amplified using known polymerase chain reaction techniques. These techniques are described for example in Saiki, et al, Primer-directed Enzymatic Amplification of DNA with a Thermostable DNA Polymerase, Science, 239, 487, 1988.

After amplification of the target gene(s), analysis is performed using standard DNA analysis techniques, such as those described in Saiki, et al, Analysis of Enzymatically Amplified Beta-globin and HLA-DQA1 with Allele Specific Oligonucleotide Probes, Nature, 324, 163, 1986.

Figure 1:
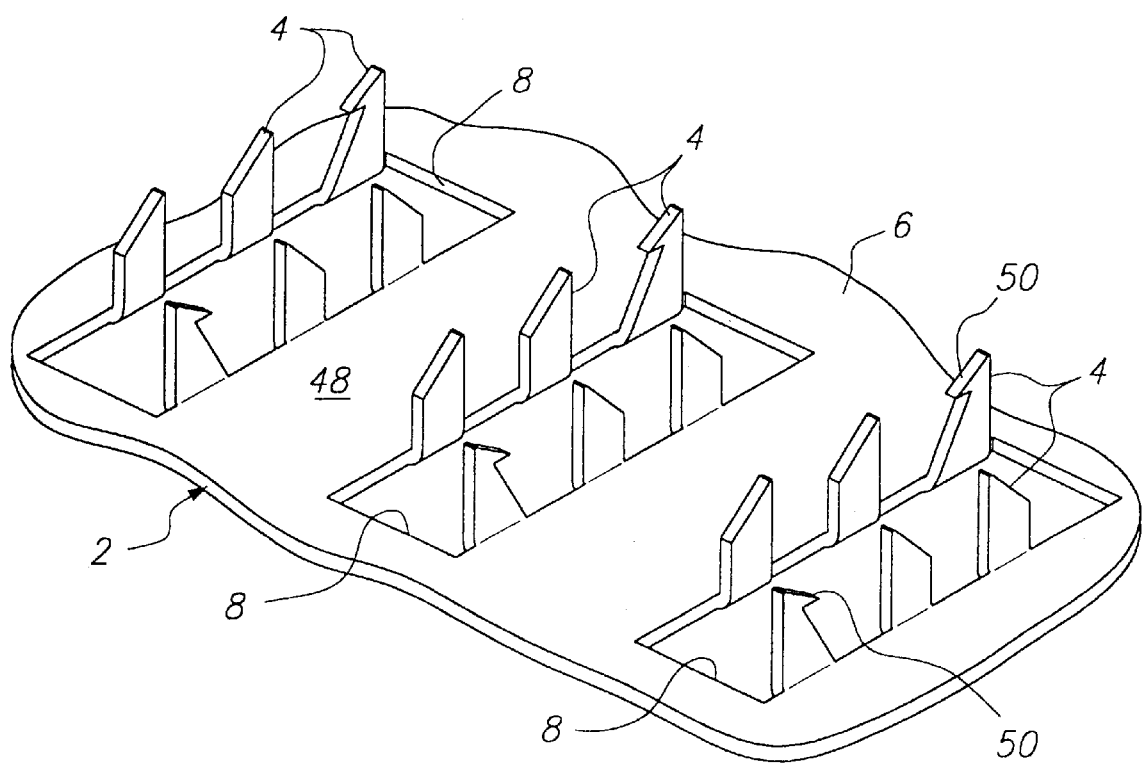
FIG. 1 is an enlarged perspective view of the skin proximal side of the microprojection array device in accordance with one embodiment of the present invention.

Turning now to the drawings in detail, one example of a skin piercing microprojection array device 2 for sampling nucleic acid according to the present invention is generally shown in FIG. 1. Device 2 comprises a plurality of microprojections 4 (i.e., a microprojection array) extending downward from one surface of a sheet or plate 6 (see FIG. 1 in which device 2 is in an inverted position to show the microprojections). The microprojections 4 penetrate through the stratum corneum layer and at least into the epidermis layer of the skin when the device is pressed against the skin to sample nucleic acid therethrough. The term "skin" as used herein refers to the skin of a living or dead animal, particularly a human, but specifically excludes mucosal membranes (e.g., the buccal mucosa). The device 2 preferably has a microprojection density of at least about 10 microprojections/cm$^2$ and more preferably at least about 50 microprojections/cm$^2$. In similar fashion, the number of openings per unit area of the plate 6 is typically at least about 10 openings/cm$^2$ and more typically at least about 100 openings/cm$^2$.

The microprojections 4 can be formed using a photoetching process, which is described in Cormier, et al. WO 97/48440, the disclosures of which are incorporated herein by reference. This process allows the microprojections 4 to be reproducibly formed on a very small (i.e., tens of microns) scale.

Figure 2:
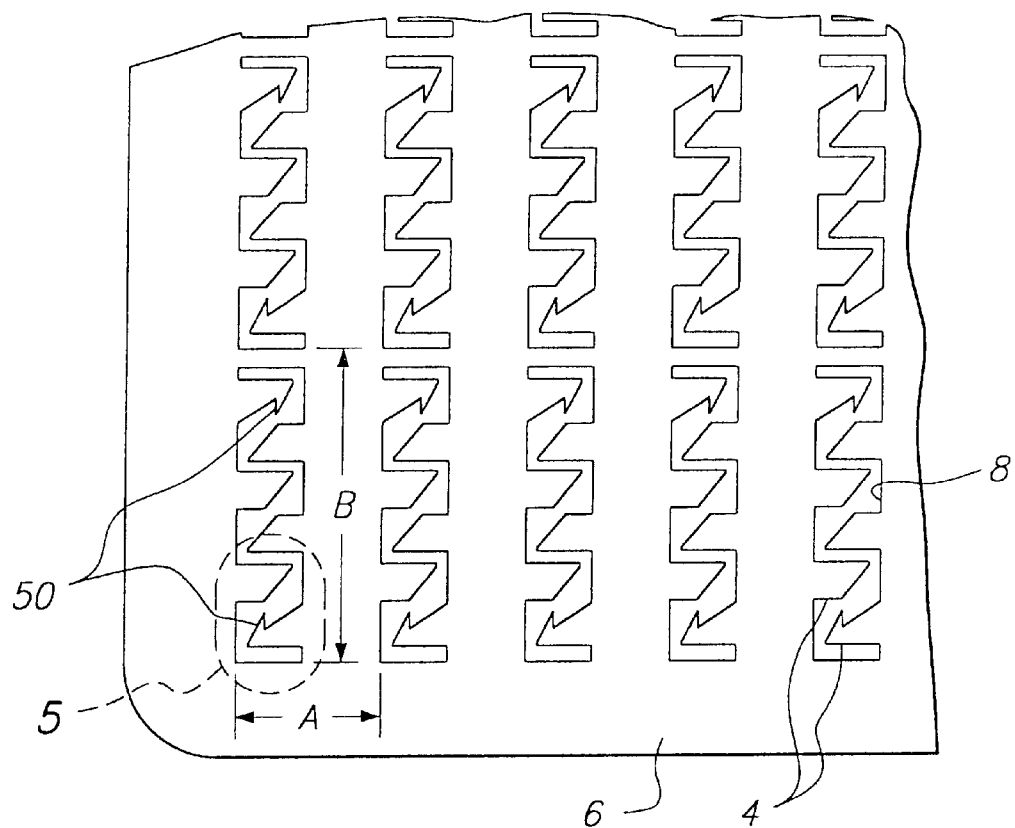
FIG. 2 is a partial top plan view of a microprojection array pattern in accordance with one embodiment of the present invention.

The plurality of microprojections 4 for puncturing the stratum corneum are present on one face surface 48 of the device 2 in any predetermined arrangement, for example, as a cluster of microprojections spaced in rows having any desired number, or in any spaced apart relation of one microprojection to each other. The device 2 of the embodiment shown in FIG. 1 is produced by the pattern shown in FIG. 2. Each microprojection has a width and thickness that facilitates penetration of the stratum corneum without bending. The required length of the microprojection is subject to variation of the skin being penetrated and corresponds to the natural thickness of the stratum corneum, for one of the principle features of the invention is that the microprojections are to penetrate the stratum corneum into the epidermis. Another factor affecting microprojection length is the method of microprojection application since the microprojections frequently do not penetrate the skin to a depth equal to the microprojection length due to the elastic properties of living animal skin. Usually, the microprojections will be about 25 $\mu$m to about 500 $\mu$m in length, with the length most typically being between about 100 $\mu$m to about 450 $\mu$m.

The pattern for any of the microprojection array devices used in the present invention may be produced with a photo-etching process. A thin sheet or plate 6 of metal such as stainless steel or titanium is etched photo-lithographically with patterns containing microblade-like structures. In general, a thin laminate dry resist or wet resist is applied on a sheet about 7 $\mu$m to about 100 $\mu$m thick, preferably about 25 $\mu$m to about 50 $\mu$m thick. The resist is contact exposed using a mask having the desired pattern and is subsequently developed. These operations are conducted in much the same way that they are for the manufacture of a printed circuit board. The sheet is then etched using acidic solutions. After the pattern has been etched through the sheet, the sheet is placed on a die having a plurality of openings corresponding to the openings 8 in the sheet. A punch having a plurality of protrusions corresponding to the openings in the sheet and die is initially located above the sheet and die. At the initial stage, the microprotrusions 4 are in the same plane as the rest of the sheet 6. The protrusions on the punch are then pressed into the openings, thus bending the microprojections 4 downward to be at an angle (e.g., substantially perpendicular) to the plane of the sheet 6 as shown in FIG. 1.

Generally, the microprojections 4 are at an angle of about 90° to the surface 48 of the sheet 6 after being punched, but they can be disposed at other angles forward or backward from the perpendicular position as long as penetration of the stratum corneum is achieved.

Another embodiment of the present invention extracts the DNA-containing intracellular and extracellular fluids from the microcuts formed by the skin piercing microprojections, wherein the fluid is extracted with a device which applys a partial vacuum to the surface of the skin. Referring now to FIG. 4, there is shown a negative pressure driven device 10 having a microprojection array device 2 on the skin proximal side of device 10. Device 10 and device 2, in combination, are used for the transdermal sampling of interstitial fluid containing nucleic acids released from the skin cells that are pierced or broken apart by the skin piercing microprojections. Device 10 is a known negative pressure (i.e., suction) applying device such as that disclosed in Ishibashi, U.S. Pat. No. 5,320,607, the disclosures of which are incorporated herein by reference. Device 10 is mounted on the skin distal surface of device 2. The skin proximal side of device 2 is in contact with the surface of skin 20, with the microprojections 4 extending at least through the stratum corneum layer of skin 20. By appropriately sealing the device 10 against the skin distal side of device 2, the negative pressure applied by device 10 causes suction to be applied through the openings 8 in sheet 6. In this manner, the nucleic acid-containing interstitial fluid is extracted out of the microcuts cut in the skin 20 and drawn into device 10.

Although it is preferred to use an uncoated microprojection array made of a sterilized metal such as stainless steel or titanium, it is possible to coat the microprojections 4 and/or the skin proximal side of plate 6 with a thin coating of a fluid absorbing material, which can absorb and hold the nucleic acid-containing fluids upon piercing the stratum corneum. It is also possible to use a nucleic acid transfer/receiving layer coating the skin proximal side of plate 6. Such transfer/receiving layers are disclosed in Theeuwes, et al. WO 98/28037, the disclosures of which are incorporated herein by reference.

The major barrier properties of the skin, such as resistance to nucleic acid efflux, reside first with the walls of individual skin cells. Thus, the microprojections in device 2 must be sized, shaped and configured to pierce through the stratum corneum layer and disrupt the cell walls of living skin cells in the layer of skin just below the stratum corneum layer, without piercing into the capillary beds within the skin so as to avoid significant bleeding. Second, the microprojections must create openings (i.e., microcuts) in the stratum corneum particularly for those embodiments which rely upon collecting the nucleic acid released from the skin cells into the interstitial fluid.

Figure 3:
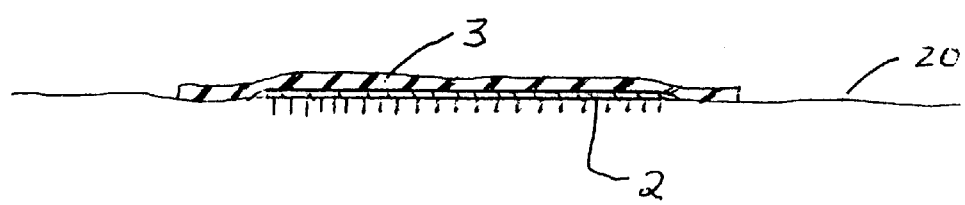
FIG. 3 is a side sectional view of a microprojection DNA-sampling array held in place on the skin with an adhesive overlay.

Because the nucleic acid-containing intracellular and extracellular fluids coat the skin-piercing microprojections substantially instanteously as the microprojections pierce the skin, there is no need to keep the microprojection array anchored or otherwise attached to the skin for any appreciable length of time. Thus, it is possible, though not necessary, to provide a conventional adhesive overlay to keep the microprojection array attached on to the skin for a short period of time. An example of such a system is disclosed in FIG. 3 with a peripheral adhesive overlay 3 maintaining device 2 in piercing relation with skin 20. In any event, the microprojection array should preferably be previously sterilized to avoid any possible cross-contamination, e.g., by picking up tissue or other nucleic acid-containing material from a source other than the test subject. Most preferably, the microprojection array and any device used to apply the microprojection array to the skin is manufactured as a single-use disposable device which is sterilized and placed in a sealed package prior to use.

The sheet and microprojections can be made from materials that have sufficient strength and manufacturability to produce microprojections, such as, glasses, ceramics, rigid polymers, metals and metal alloys. Examples of metals and metal alloys include but are not limited to titanium, stainless steel, iron, steel, tin, zinc, copper, platinum, aluminum, germanium, nickel, zirconium, and titanium alloys consisting of nickel, molybdenum and chromium, metals plated with nickel, gold, rhodium, iridium, titanium, platinum, and the like. Examples of glasses include silicon and a devitrified glass such as "Photoceram" available from Corning in Corning, N.Y. Examples of rigid polymers include but are not limited to polystyrene, polymethylmethacrylate, polypropylene, polyethylene, "Bakelite", cellulose acetate, ethylcellulose, styrene/acrylonitrile copolymers, stryrenetbutadiene copolymers, acrylonitrile/butadiene/styrene (ABS) copolymers, polyvinyl chloride and acrylic acid polymers including polyacrylates and polymethacrylates. Most preferably, the sheet and microprojections are made from titanium or stainless steel.

The number of microblades and openings of any of the embodiments of the device 2 is variable with respect to the desired DNA sample size and whether or not a negative pressure driven sampling device is used, and other factors as will be evident to one of ordinary skill in the art. The following examples illustrate the uses and advantages of the present invention.

EXAMPLE 1

Studies are performed in two siblings and four unrelated individuals. In each subject, the treatment site (ventral forearm) is cleaned with a 70% sterile isopropyl alcohol pad. The skin site is then dried with a sterile gauze pad. The skin is pierced by impacting a microprojection device against the skin surface using a spring-loaded applicator. The microprojection device includes a 1 $cm^2$ disk-shaped microprojection array having microprojections with a length of 200 $\mu$m and a density of 320 microprojections/$cm^2$, adhered to a low density polyethylene backing with polyisobutylene adhesive. Following application, the system is immediately removed with sterile forceps and is transferred into a sterile vial and is stored frozen (−20° C.) until analysis. In the same subjects, additional DNA samples are obtained by swabbing the inside of the cheek for 30 seconds with a cytobrush which is immediately transferred into a sterile vial and stored frozen (−20° C.) until analysis.

For analysis, the vials are sent to a contract laboratory specialized in DNA profiling. The DNA is extracted using standard procedures. Polymorphism for the gene DQA1 is assessed by PCR and reverse dot blot hybridization procedure. Results demonstrate that the two siblings are indeed related whereas the remaining individuals are unrelated to all. Identical results are obtained with the cytobrushes.

These results demonstrate the validity of the new nucleic acid sampling method. Applications include forensics, parenthood analysis, genetic testing for predisposition to genetic diseases and detection of infectious diseases.

While the invention has been described in conjunction with the preferred specific embodiments thereof, it is to be understood that the foregoing description as well as the example are intended to illustrate and not limit the scope of the invention. Other aspects, advantages and modifications within the scope of the invention will be apparent to those skilled in the art to which the invention pertains.

What is claimed is:

1. A method of transdermally sampling nucleic acid comprising:

piercing through the stratum corneum layer of skin into at least an underlying epidermis layer with a skin-piercing microprojection, disrupting or dislodging skin cells containing nucleic acid; collecting the nucleic acid from the disrupted or dislodged skin cells by allowing the microprojection to become at least partially coated with nucleic acid-containing body fluid, withdrawing from the skin the microprojection and the nucleic acid-containing body fluid coated thereon; removing at least some of the nucleic acid from the microprojection and analyzing the nucleic acid removed from the withdrawn microprojection.

2. A method of transdermally sampling nucleic acid comprising:

piercing through the stratum corneum layer of skin into at least an underlying epidermis layer to a depth of less than about 500 μm with a skin-piercing microprojection, disrupting or dislodging skin cells containing nucleic acid, collecting the nucleic acid from the disrupted or dislodged skin cells by allowing the microprojection to become at least partially coated with nucleic acid-containing body fluid, withdrawing from the skin the microprojection and the nucleic acid-containing body fluid coated thereon: removing at least some of the nucleic acid from the microprojection; and analyzing the nucleic acid removed from the withdrawn microprojection.

3. A method of transdermally sampling nucleic acid comprising:

piercing through the stratum corneum layer of skin into at least an underlying epidermis layer with a plurality of skin-piercing microprojections and disrupting or dislodging skin cells containing nucleic acid; collecting the nucleic acid from the disrupted or dislodged skin cells by allowing at least one of the microprojections to become at least partially coated with nucleic acid-containing body fluid; withdrawing from the skin the microprojections and the nucleic acid-containing body fluid coated thereon: removing at least some of the nucleic acid from the microprojection; and analyzing the nucleic acid removed from the withdrawn microprojections.

4. A method of transdermally sampling nucleic acid comprising:

piercing through the stratum corneum layer of skin into at least an underlying epidermis layer with a multiplicity of skin-piercing microprojections and disrupting or dislodging skin cells containing nucleic acid; collecting the nucleic acid from the disrupted or dislodged skin cells by allowing at least one of the microprojections to become at least partially coated with nucleic acid-containing body fluid; withdrawing from the skin the microprojections and the nucleic acid-containing body fluid coated thereon; removing at least some of the nucleic acid from the microprojections; and analyzing the nucleic acid removed from the withdrawn microprojections.

5. A method of transdermally sampling nucleic acid comprising:

piercing through the stratum corneum layer of skin to a depth of at least about 25 μm and into at least an underlying epidermis layer with a skin-piercing microprojection, disrupting or dislodging skin cells containing nucleic acid; collecting the nucleic acid from the disrupted or dislodged skin cells by allowing the microprojection to become at least partially coated with nucleic acid-containing body fluid; withdrawing from the skin the microprojection and the nucleic acid-containing body fluid coated thereon; removing the nucleic acid from the microprojection; and analyzing the nucleic acid removed from the withdrawn microprojection.

6. A method of transdermally sampling nucleic acid comprising:

piercing through the stratum corneum layer of skin into at least an underlying epidermis layer with an array of skin-piercing microprojections, the array having a microprojection density of at least about 10 microprojections/cm$^2$, disrupting or dislodging skin cells containing nucleic acid; collecting the nucleic acid from the disrupted or dislodged skin cells by allowing the array of microprojections to become at least partially coated with nucleic acid-containing body fluid; withdrawing from the skin the array of microprojections and the nucleic acid-containing body fluid coated thereon; removing the nucleic acid from the microprojections; and analyzing the nucleic acid removed from the withdrawn microprojection array.

7. The method of any of claim 1 or 2–6, wherein the step of analyzing the nucleic acid comprises the polymerase chain reaction assay.

8. The method of any of claims 1 to 2 or 5–9, wherein the skin is the skin of a human.

9. The method of any of claim 1 or 2–6, wherein the nucleic acid is selected from the group consisting of DNA, DNA fragments, RNA, RNA fragments, genes, chromosomes, and polynucleic acid sequences.

* * * * *